(12) United States Patent
Remon et al.

(10) Patent No.: US 9,168,303 B2
(45) Date of Patent: Oct. 27, 2015

(54) INTRAVAGINAL DELIVERY SYSTEM

(75) Inventors: Jean Paul Remon, Melle (BE); Chris Vervaet, Kachtem (BE); Hans Verstraelen, Merelbeke (BE); Marleen Temmerman, Eksaarde (BE)

(73) Assignee: Universiteit Gent, Gent (BG)

( * ) Notice: Subject to any disclaimer, the term of this patent is extended or adjusted under 35 U.S.C. 154(b) by 0 days.

(21) Appl. No.: 14/131,495

(22) PCT Filed: Jul. 12, 2012

(86) PCT No.: PCT/EP2012/063702
§ 371 (c)(1),
(2), (4) Date: Jan. 8, 2014

(87) PCT Pub. No.: WO2013/010915
PCT Pub. Date: Jan. 24, 2013

(65) Prior Publication Data
US 2014/0154293 A1 Jun. 5, 2014

(30) Foreign Application Priority Data
Jul. 15, 2011 (EP) .................................. 11174103

(51) Int. Cl.
*A61K 47/32* (2006.01)
*A61K 9/00* (2006.01)
*A61K 31/19* (2006.01)
*A61K 47/38* (2006.01)

(52) U.S. Cl.
CPC ............... *A61K 47/32* (2013.01); *A61K 9/0036* (2013.01); *A61K 31/19* (2013.01); *A61K 47/38* (2013.01)

(58) Field of Classification Search
USPC ........................................................ 424/430
See application file for complete search history.

(56) References Cited

U.S. PATENT DOCUMENTS

| | | | | |
|---|---|---|---|---|
| 5,543,150 A | * | 8/1996 | Bologna et al. | ................ 424/430 |
| 2007/0196433 A1 | | 8/2007 | Ron et al. | |
| 2014/0074067 A1 | * | 3/2014 | Kiser et al. | .................... 604/515 |

FOREIGN PATENT DOCUMENTS

| WO | 2006065873 A2 | 6/2006 |
|---|---|---|
| WO | 2009066006 A1 | 5/2009 |
| WO | 2009066006 A1 * | 5/2009 |
| WO | WO 2009066006 A1 * | 5/2009 |
| WO | WO 2009129459 A1 * | 10/2009 |
| WO | 2010133761 A1 * | 11/2010 |
| WO | 2010133761 A1 | 11/2010 |
| WO | WO 2010133761 A1 * | 11/2010 |

OTHER PUBLICATIONS

Andersch et al., "Bacterial Vaginosis and the Effect of Intermittent Prophylactic Treatment with an Acid Lactate Gel", Gynecol Obstet Invest, vol. 30, pp. 114-119, Feb. 16, 1990.
Boskey et al., "Origins of vaginal acidity: high D/L lactate ratio is consistent with bacteria being the primary source", Human Reproduction, vol. 16, No. 9, pp. 1809-1813, May 8, 2001.
Search Report and Written Opinion for PCT/EP2012/063702 dated Sep. 10, 2012.

* cited by examiner

*Primary Examiner* — Robert A Wax
*Assistant Examiner* — Melissa Mercier
(74) *Attorney, Agent, or Firm* — Dinsmore & Shohl LLP (57) ABSTRACT

The present invention in general relates to an intravaginal delivery system as well as uses thereof and methods for manufacturing and use of the same. In particular the present invention relates to an intravaginal delivery system for the controlled release of one or more organic acids, such as lactic acid; said intravaginal delivery system being characterized in that it comprises a combination of ethylene vinyl acetate (EVA) copolymers and carboxylic polymers, such as for example methacrylic acid-methacrylic ester copolymers.

16 Claims, 1 Drawing Sheet

INTRAVAGINAL DELIVERY SYSTEM

FIELD OF THE INVENTION

The present invention in general relates to an intravaginal delivery system as well as uses thereof and methods for manufacturing and use of the same.

In particular the present invention relates to an intravaginal delivery system for the controlled release of one or more organic acids, such as lactic acid; said intravaginal delivery system being characterized in that it comprises a combination of ethylene vinyl acetate (EVA) copolymers and carboxylic polymers, such as for example methacrylic acid-methacrylic ester copolymers.

BACKGROUND TO THE INVENTION

The vagina is a fibromuscular tubular tract leading from the uterus to the exterior of the body in females. A healthy vagina is colonized by a mutually symbiotic flora of microorganisms, in particular lactobacilli, that protect its host from vaginal infections. The acidity of a healthy vagina of a woman of child-bearing age (pH about 3.8-4.5) is due to the degradation of secreted glycogen/glucose to lactic acid and acetate by lactobacilli (Boskey et al., 2001). Said acidity being unfavourable for the growth of many pathogenic microorganisms, including bacteria, protozoa and viruses. However, any imbalance in said vaginal ecosystem may result in overgrowth of pathogenic microorganisms, resulting in vaginal infections.

Multiple kinds of vaginal infections (vaginitis) exist, depending on the pathogenic microorganism involved such as bacterial vaginosis, vaginal candidiasis and trichomoniasis and combinations thereof.

Bacterial vaginosis is the most common cause of vaginal infections, and is associated with complications during pregnancy as well as an increased risk for sexually transmitted diseases. It is caused by an imbalance of naturally occurring bacterial flora, wherein the lactobacilli are overgrown by a mixed flora of anaerobic bacteria. Amongst other diagnostic criteria, a pH greater than 4.5 is considered to be suggestive of bacterial vaginosis. Current treatment options rely on oral or vaginal administration of classical antibiotics such as metronidazole and clindamiycine, however there is a rate of recurrence of over 50% within 3 months after the first exposure (Verstraeten & Verhelst, 2009). Alternative treatment options include acidification of the vagina with naturally occurring acids such as lactic acid or acetate. For example, Andersch et al. treated 42 women having recurrent bacterial vaginosis, with an intravaginal lactic acid gel. After 6 months of treatment 88% of women from the treated group had a normal vaginal microflora in contrast to 16% of women in the placebo group (Andersch et al., 1990).

Vaginal candidiasis is a fungal infection of any of the Candida species (yeasts), of which Candida albicans is the most common. Most candidial infections are treatable and result in only minimal complications such as redness or itching, however complications may also be severe or even fatal if left untreated in certain populations such as immuno-compromised patients. External use of detergents or internal disturbances (hormonal or physiological) can disturb the normal vaginal flora and result in an overgrowth of Candida cells causing infection. Also pregnancy and the use of oral contraceptives have been reported as risk factors. In clinical settings, candidiasis is commonly treated with antimycotics such as clotrimazole, nystatin, fluconazole and ketoconazole. However, C. albicans can develop resistance to said antimycotic drugs, so alternative treatment options are desired.

Trichomoniasis is a sexually transmitted disease of the urogenital tract and is caused by the single-celled protozoan parasite Trichomonas vaginalis. Symptoms include inflammation of the cervix, urethra and vagina, which produce an itching and burning sensation. Current treatment options include the use of the antibiotic/anti-protozoal (metronidazole) or anti-parasitic (tinidazole) drugs. However, as with most anti-microbial drugs, resistance may occur, thereby underscoring the need for alternative treatment options.

Therefore, alternative treatment options, not making use of antibiotics or other kinds of drugs, for vaginal infections and sexually transmitted diseases have been suggested and may reside in the application of acidic compounds (for lowering the pH) or naturally occurring vaginal bacterial strains. However, most currently available products make use of gel-like formulations requiring multiple daily applications, requiring a lot of effort and commitment of the patient. It would therefore be highly advantageous to provide a controlled-release product, for delivery of active ingredients, in particular organic acids, thereby no longer requiring multiple applications per day, but for example only once every few days or even once every few weeks.

It was therefore an object of the present invention to provide an intravaginal delivery system for the controlled release of organic acids, in particular lactic acid.

Although intravaginal delivery systems for the controlled release of active ingredients have been described before, most of them do not comprise organic acids as an active ingredient.

For example WO2006065873 provides an intravaginal flat porous mesh encircled with a fiber-reinforced composite ring, said ring comprising an elastomeric copolymeric matrix, such as for example glycolide copolymers, carbonate copolymers and silicone polymers. This porous mesh is provided for the controlled delivery of at least one bioactive agent. Furthermore, any organic acid present in the device is merely used as an excipient in addition to the bioactive agent(s), not as an active ingredient itself (e.g. example 10 of WO2006065873). US20070196433 provides a two-segmental drug delivery device comprising a drug-permeable polymeric substance, such as for example an ethylene-vinyl acetate copolymer. However, again, amongst the active ingredients no organic acids are mentioned, but they rather include pharmaceutical drugs, such as antibiotics. WO2009066006 provides an intravaginal delivery system for the controlled release of pharmaceuticals, in particular drospirenone and estradiol, said delivery system comprising one or more polymers selected from a long list of possibilities. However, the only exemplified delivery system comprises the commonly used PEO-b-PDMS (polyethyleneoxide-b-poly (dimethylsiloxane)) copolymer. Again, this delivery system may further comprise organic acids, but none of the exemplified systems comprises one or more organic acids as the main active ingredient.

WO2010133761 provides an intravaginal polymeric delivery system comprising at least one active ingredient, including acidic compounds or beneficial microorganism. However, again suitable polymers may be selected from a long list of possible polymers including combinations thereof, with the only exemplified polymer combination being the commonly used PEO-b-PDMS (polyethyleneoxide-b-poly (dimethylsiloxane)) copolymer.

Evidently, when trying to incorporate pharmaceutically relevant levels of organic acids in a certain polymeric environments, it is not to be excluded that one may encounter undesired reactivity. Furthermore, in order to achieve a controlled release of the organic acid from the delivery system, the polymeric environment should not only be compatible with the presence of pharmaceutically relevant levels of organic acids, but also allow a controlled release from the delivery device. Therefore, one cannot simply take any available intravaginal delivery system and replace the used active ingredient by a pharmaceutically relevant concentration of one or more organic acids.

To the best of our knowledge, only 1 publication describes an intravaginal delivery system comprising organic acid(s) as the main active ingredient (WO2010/133761). In this publication, only the commonly used PEO-b-PDMS (polyethyleneoxide-b-poly (dimethylsiloxane)) copolymer was used and folic acid was incorporated therein (example 1). However, no data regarding the release profile of said folic acid are provided, questioning whether this device would be useful for the controlled release of organic acids. Furthermore, as evident from the examples hereinafter, cationic polymers, have been found not to be useful for preparing a controlled release delivery system.

In contrast, we have found that a delivery system comprising one or more EVA (ethylene vinyl acetate) copolymers and one or more carboxylic polymers is very suitable for the controlled release of organic acids.

SUMMARY OF THE INVENTION

In a first objective, this invention provides an intravaginal delivery system for the controlled release of one or more organic acids, said delivery system being characterized in that it comprises a combination of one or more ethylene vinyl acetate (EVA) copolymers and one or more carboxylic polymers.

In a particular embodiment of this invention, said one or more EVA copolymers are copolymers of ethylene and vinyl acetate, comprising about and between 25 to 40% vinyl acetate; in particular about 40% vinyl acetate.

In a further particular embodiment, said one or more carboxylic polymers are selected from the list consisting of methacrylic acid copolymers, cellulose phthalates, carbopol, alginates, polylactic acids, hypromellose acetate succinates (HPMCAS), and copolymers thereof; in particular methacrylic acid copolymers.

In a preferred embodiment, the intravaginal delivery system according to this invention comprises a combination of one or more EVA copolymers, in particular EVA40; and one or more methacrylic acid copolymers, in particular methacrylic acid-methacrylic ester copolymers.

In yet a further embodiment, the one or more organic acids are selected from the group consisting of lactic acid, polylactic acid, glycolic acid, polyglycolic acid, ascorbic acid, folic acid, p-aminobenzoic acid, alginic acid, sorbic acid, tartaric acid, acetic acid, formic acid citric acid, oxalic acid, uric acid, edetic acid and the like; in particular lactic acid and polylactic acid.

In a specific embodiment, the intravaginal delivery system according to this invention comprises between and about 1-20% wt of said one or more organic acids; in particular comprising about 5% wt of said one or more organic acids.

In another specific embodiment, the intravaginal delivery system according to this invention comprises about and between 65-75% wt of one or more EVA polymers and about 20% wt of one or more carboxylic polymers.

In a preferred embodiment, the intravaginal delivery system according to this invention comprises about and between 5-10% wt lactic acid, about and between 70-75% wt EVA and about and between 15-30% of one or more carboxylic polymers.

The intravaginal delivery system according to this invention may be manufactured by any suitable method, in particular by extrusion, co-extrusion and/or injection molding.

The intravaginal delivery system according to this invention, may further comprise one or more pharmaceutically active ingredients.

In a further aspect, the present invention provides a method for the controlled intravaginal delivery of one or more organic acids, said method comprising the administration of an intravaginal delivery system according to this invention.

In a specific embodiment, this invention provides a method of preventing and/or treating vaginal infections, in particular bacterial infections; said method comprising administering to a patient in need thereof, an intravaginal delivery system according to this invention.

This invention further provides an intravaginal delivery system according to this invention for use as a medicament, in particular for use in the controlled intravaginal delivery of one or more organic acids, either or not in combination with one or more additional active agents.

Thus, the current invention provides an intravaginal delivery system according to this invention for use in preventing and/or treating vaginal infections, in particular bacterial infections; more in particular recurrent vaginitis.

Said intravaginal delivery system may be used in combination with the administration of one or more additional active agents, for use in preventing and/or treating vaginal infections, in particular bacterial infections; more in particular recurrent vaginitis.

DETAILED DESCRIPTION OF THE INVENTION

In a first aspect, the present invention provides an intravaginal delivery system for the controlled release of one or more organic acids, said delivery system being characterized in that it comprises a combination of one or more ethylene vinyl acetate (EVA) copolymers and one or more carboxylic polymers.

As used in the context of this invention, an intravaginal delivery system is meant to include any device suitable for providing the intravaginal controlled delivery of one or more organic acids, and capable of being prepared by a combination of one or more ethylene vinyl acetate (EVA) copolymers and one or more carboxylic polymers. Said delivery system may be in any suitable form such as for example vaginal pessaries or vaginal rings. A vaginal ring is inserted in the vagina and the vaginal wall holds it in place, where it may remain over the complete period of organic acid release therefrom.

The delivery system according to this invention can have many shapes, for example annular, ring-shaped, oval, spiral, ellipse, toroidal and the like. Therefore, as used herein the term vaginal ring, is also meant to include intravaginal devices having other than ring-like shapes.

The delivery system according to this invention can be manufactured in any size required, depending on the patient, amount of organic acid delivery required, particular application, etc. In general for an adult human female, a vaginal ring may typically have a ring diameter of about and between 35-70 mm, preferably about and between 40-65 mm, most preferably about and between 50-55 mm. The cross-sectional diameter is preferably about and between 2.0-6.0 mm, more preferably about and between 3.5 and 5.0 mm, in particular about 4.0 mm.

As used herein 'controlled release' means to include any type of release, which is not an immediate release. For example, the release of organic acids from the intravaginal delivery system according to this invention may be slow and spread over a certain period in time, in order to maintain a certain pH in the vagina. More in particular, the delivery system allows a sustained release of an organic acid over a period of up to 20 days, more specific, up to 7, 10, 14, or 18 days. Said intravaginal delivery system as such does not have to be replaced multiple times a day, as is the case for intravaginal gels, but can in general be replaced after one or more days, such as every week or once every 2 weeks, or even every 1-4 weeks, in particular every week or once every 2 weeks.

As used herein EVA (ethylene vinyl acetate) copolymers are copolymers of ethylene and vinyl acetate, wherein the weight percent vinyl acetate usually varies from 10 to 40%, the remainder being ethylene. EVA copolymers are in particular soft, flexible and easily processable, and are therefore very suitable for the preparation of intravaginal delivery systems. The intravaginal delivery system according to this invention, in particular comprises about and between 25-40% vinyl acetate, more preferably about 30 or 40%. The intravaginal delivery system according to this invention may comprise any suitable amount of EVA polymers, but preferably comprises about and between 65-80% wt of one or more EVA polymers.

As used herein, carboxylic polymers are meant to include polymers comprising one or more carboxylic (—COOH) functional groups. Said carboxylic polymers are preferably selected from the list consisting of methacrylic acid (co) polymers, cellulose acetate phthalates (CAP), acrylic acid (co)polymers, alginates (alginic acids), polylactic acids, hypromellose acetate succinates (HPMCAS), copolymers or mixtures thereof, and the like; in particular methacrylic acid copolymers. Examples of said carboxylic methacrylic acid copolymers include but are not limited to methacrylic acid copolymers L (commercially available under the tradename Eudragit® L) and methacrylic acid copolymers S (commercially available under the tradename Eudragit® S.

The intravaginal delivery system according to this invention may comprise any suitable amount of carboxylic polymers, but comprises in particular about and between 10-50% wt of one or more carboxylic polymers, and more in particular about 20% wt of one or more carboxylic polymers.

In a particular embodiment, the intravaginal delivery system according to this invention, comprising about and between 65-75% wt of one or more EVA polymers and about 20% wt of one or more carboxylic polymers.

An organic acid as used herein is meant to be an acidic compound, i.e. with a $pK_a<6$, preferably <5 (at 25° C.), which contains carbon, oxygen and hydrogen. Preferably, the organic acids according to this invention are carboxylic acids, including $C_2$-$C_6$ mono-, di- or tri-carboxylic acids, such as those selected from the list consisting of lactic acid, polylactic acid, glycolic acid, polyglycolic acid, ascorbic acid, folic acid, p-aminobenzoic acid, alginic acid, sorbic acid, tartaric acid, acetic acid, formic acid citric acid, oxalic acid, uric acid, edetic acid, adipic acid, succinic acid, and glutamic acid, or mixtures thereof, and the like; preferably lactic acid and polylactic acid. The intravaginal delivery system according to this invention may comprise any suitable amount of said one or more organic acids; but preferably comprises about and between 1-20% wt of said one or more organic acids; in particular about 5, 6, 7, 8, 9 or 10% wt. The organic acid can be in a solid or liquid state, but the intravaginal delivery system of the present invention is particularly useful for the delivery of organic acids in the liquid state.

In a preferred embodiment, the intravaginal delivery system according to this invention comprises about and between 5-10% wt lactic acid, about and between 70-75% wt EVA and about and between 15-30% of one or more carboxylic polymers. In a specific embodiment, the intravaginal delivery system according to this invention comprises about and between 5-10% wt organic acid, in particular lactic acid, about and between 70-75% wt EVA, in particular EVA40 or EVA28, and about 20% of methacrylic acid copolymer L or cellulose acetate phthalates (CAP).

The intravaginal delivery system according to this invention may be prepared by any suitable method. In general, the organic acid is homogenized together with the one or more EVA polymers and the one or more carboxylic polymers followed by extrusion at about and between 60-160° C., in particular at about 90° C. Thereafter, the material is processed to the desired shape by moulding, injection moulding, rotation/injection moulding, casting, extrusion, co-extrusion, coating extrusion and/or blend-extrusion or other appropriate methods. In particular the intravaginal delivery system is manufactured by extrusion, co-extrusion or injection molding. More detailed methods for preparing an intravaginal delivery system according to this invention are further provided in the examples hereinafter.

The intravaginal delivery system according to this invention comprises one or more organic acids at therapeutically relevant levels, but it may further comprise additional pharmaceutically active ingredients, in particular those useful for the treatment of vaginal infections. Alternatively, the intravaginal delivery system comprises one or more organic acids as the sole active ingredient, and in parallel to the administration of said delivery system, a patient in need thereof may further be treated separately with one or more additional pharmaceutically active ingredients.

A further aspect of this invention is to provide a method for the controlled intravaginal delivery of one or more organic acids, said method comprising the administration of an intravaginal delivery system according to this invention. It in particular provides a method of preventing and/or treating vaginal infections, in particular bacterial infections; especially recurrent vaginitis. Alternatively the intravaginal delivery system may also be used for preventing and/or treating fungal infections, and/or sexually transmitted diseases.

As used herein vaginitis is meant to include any infection of the vagina. In general vaginitis is defined as a spectrum of conditions causing vulvovaginal symptoms such as itching, burning, irritation, and abnormal discharge. Vaginitis according to this invention, in particular includes bacterial vaginiosis, more in particular of the recurrent type. Patients having recurrent vaginitis, need regular daily treatments and therefore in particular benefit from a controlled release intravaginal delivery device, that can remain in place and deliver pharmaceutically active agents, such as lactic acid, for a longer period of time.

The intravaginal delivery systems according to this invention are in particular suitable for use as a medicament, in particular for use in preventing and/or treating vaginal infections, such as bacterial infections; especially recurrent vaginitis; and for the controlled intravaginal delivery of one or more organic acids.

EXAMPLES

Example 1

Preparation and Testing of Cationic Polymer Containing Delivery Systems

In this first example, we evaluated whether cationic polymers are suitable for preparing a controlled release delivery system for organic acids.

Therefore, a mixtures of 75%-wt ethylene vinyl acetate (EVA), 20%-wt aminoalkyl methacrylate copolymer E (Eudragit E), and 5%-wt lactic acid was homogenized and fed into a co-rotating twin-screw mini-extruder at 90° C. and 60 rmp. The extrudates were cooled down to room temperature and manually cut, using surgical blades, into extrudates of 4.5 cm for pH monitoring tests.

A 4.5 cm extrudate was placed in a closed vessel in 3 ml demi-water of which the pH was initially measured. The vessel was kept at 37° C.+/−0.5° C. and every 24 h, during 4 consecutive days, the pH was measured and replaced by 3 ml fresh demi-water (pH determined in advance). The results of this experiment are shown in table 1.

TABLE 1 pH determination

| | Day | | | |
|---|---|---|---|---|
| | 1 | 2 | 3 | 4 |
| Initial pH | 4.5 | 4.6 | 4.8 | 4.2 |
| After 24 h | 5.3 | 5.3 | 5.2 | 6.0 |

As evident from table 1, in comparison with the initial pH, the pH after each period of 24 h increased, whereas based on the fact that lactic acid was incorporated, a decrease was expected. These data therefore indicate that cationic polymers, such as Eudragit E, are not suitable for preparing a controlled release delivery system for organic acids, such as lactic acid.

Example 2

Preparation and Testing of Carboxylic Acid Polymer Containing Delivery System As evident from example 1, cationic polymers are not suitable for preparing a controlled delivery system for organic acids, therefore in this example, we evaluated whether carboxylic acid containing polymers were suitable for said purpose.

2.1. Physical mixtures of different quantities of ethylene vinyl acetate (EVA), methacrylic acid-methyl methacrylate copolymer (Eudragit® L), and lactic acid were homogenized and fed into a co-rotating twin-screw mini-extruder at 90° C. and 60 rmp. The extrudates were cooled down to room temperature and manually cut, using surgical blades, into extrudates of 4.5 cm for pH monitoring tests.

A 4.5 cm extrudate was placed in a closed vessel in 3 ml demi-water of which the pH was initially measured. The vessel was kept at 37° C.+/−0.5° C. and every 24 h, during 10-13 consecutive days, the pH was measured and replaced by 3 ml fresh demi-water (pH determined in advance). Three different compositions were tested:

1. Placebo extrudate: 80% EVA and 20% Eudragit L
2. Extrudate A: 75% EVA, 20% Eudragit L and 5% lactic acid
3. Extrudate B: 70% EVA, 20% Eudragit L and 10% lactic acid

TABLE 2 pH determination

| | | Day | | | | | | | | | | | | |
|---|---|---|---|---|---|---|---|---|---|---|---|---|---|---|
| | | 1 | 2 | 3 | 4 | 5 | 6 | 7 | 8 | 9 | 10 | 11 | 12 | 13 |
| Placebo | Initial pH | 6.9 | 6.3 | 6.7 | 5.7 | 6.7 | 6.7 | 6.0 | 6.7 | 5.9 | 6.0 | N/A | N/A | N/A |
| | After 24 h | 7.8 | 8.0 | 7.7 | 7.5 | 8.7 | 8.8 | 8.7 | 8.5 | 8.7 | 8.7 | N/A | N/A | N/A |
| Extr. A | Initial pH | 6.9 | 6.3 | 6.7 | 5.7 | 6.7 | 6.7 | 6.0 | 6.7 | 5.9 | 6.0 | 6.0 | N/A | N/A |
| | After 24 h | 3.0 | 3.1 | 3.2 | 2.9 | 3.5 | 3.7 | 3.7 | 3.7 | 4.0 | 4.0 | 5.0 | N/A | N/A |
| Extr. B | Initial pH | 6.0 | 6.4 | 6.0 | 6.1 | 6.2 | 6.9 | 6.3 | 6.7 | 6.7 | 6.7 | N/A | 6.0 | 6.7 |
| | After 24 h | 2.5 | 2.5 | 2.4 | 2.7 | 2.9 | 3.3 | 3.2 | 3.3 | 4.4 | 4.5 | N/A | 5.4 | 5.5 |

As evident from table 2, in contrast to the placebo extrudate wherein the pH slightly increased over every period of 24 h, both for extrudate A as well as extrudate B a significant decrease in pH over every period of 24 h was observed, indicating that lactic acid is indeed released from the extrudates. Furthermore, even after 10-13 days lactic acid appears to be released from the extrudates.

2.2. A physical mixture of 70% ethylene vinyl acetate 28HV (EVA28HV), 20% cellulose acetate phthalates (CAP), and 10% acetic acid was homogenized and fed into a co-rotating twin-screw mini-extruder at 90° C. and 60 rmp. The extrudates were cooled down to room temperature and manually cut, using surgical blades, into extrudates of 4.5 cm for pH monitoring tests.

1. The extrudate was placed on a closed vessel in 3 ml demi water;
2. Initial pH was measured;
3. After 24 u the pH was measured and the medium was replaced with fresh demi water.

Sample 1: 181.8 mg in 3 ml demi water

| | Day | | | | | |
|---|---|---|---|---|---|---|
| | 1 | 2 | 3 | 4 | 5 | 6 |
| Initial pH | 3.9 | 3.95 | 4.20 | 4.36 | 4.64 | 5.21 |
| After 24 h | 3.03 | 3.41 | 3.59 | 3.63 | 3.91 | 4.15 |

Sample 2: 189.2 mg in 3 ml demi water

|  | Day | | | | | |
|---|---|---|---|---|---|---|
|  | 1 | 2 | 3 | 4 | 5 | 6 |
| Initial pH | 3.8 | 3.73 | 4.05 | 4.37 | 4.99 | 4.99 |
| After 24 h | 3.04 | 3.33 | 3.55 | 3.58 | 3.84 | 4.06 |

Sample 3: 350.4 mg in 6 ml demi water

|  | Day | | | | | |
|---|---|---|---|---|---|---|
|  | 1 | 2 | 3 | 4 | 5 | 6 |
| Initial pH | 3.7 | 3.96 | 4.32 | 4.42 | 5.05 | 5.12 |
| After 24 h | 3.0 | 3.41 | 3.54 | 3.64 | 3.85 | 4.00 |

As evident from the data, the pH decreased over every period of 24 h, indicating that acetic acid is indeed released from the extrudate. Furthermore, even after 6 days acetic acid is released from the extrudate.

2.3. These data therefore indicate that, in contrast to cationic polymers, carboxylic acid containing polymers are suitable for preparing a controlled release delivery system for organic acids, such as lactic acid and acetic acid. Said polymers not only provide controlled release of the acid, but also allow to incorporate sufficiently high organic acid levels making a release over a longer period of time possible.

Example 3

Slug Irritation Test

Study Outline:

The Slug Mucosal Irritation (SMI) assay was initially developed at the Laboratory of Pharmaceutical Technology (UGent) to predict the mucosal irritation potency of pharmaceutical formulations and ingredients. The test utilizes the terrestrial slug *Arion lusitanicus*. The body wall of the slugs is a mucosal surface composed of different layers. The outer single-layered columnar epithelium that contains cells with cilia, cells with microvilli and mucus secreting cells covers the subepithelial connective tissue. Slugs that are placed on an irritating substance will produce mucus. Additionally tissue damage can be induced which results in the release of proteins and enzymes from the mucosal surface. Several studies have shown that the SMI assay is a useful tool for evaluating the local tolerance of pharmaceutical formulations and ingredients (Adriaens et al., 1999; Adriaens et al., 2001; Callens et al., 2001; Ceulemans et al., 2001; Adriaens et al., 2003; Dhondt et al., 2004; Weyenberg et al., 2004; Dhondt et al., 2005). A classification prediction model that distinguishes between irritation (mucus production) and tissue damage (release of proteins and enzymes) has been developed (Adriaens et al., 2004).

The test was 'in house' validated using reference chemicals for eye irritation (ECETOC eye reference data bank). These studies have shown that the SMI assay can be used as an alternative to the in vivo eye irritation tests (Draize et al., 1944; Adriaens et al., 2002; Adriaens et al., 2005; Dhondt et al., 2005). Moreover, a multi-center prevalidation study with four participating laboratories showed that the SMI assay is a relevant, easily transferable and reproducible alternative to predict the eye irritation potency of chemicals (Adriaens et al., 2008).

Purpose of the Study:

The purpose of this assay is to assess the irritancy potential of the test items as detailed below. Using the objective values obtained for the parameter (mucus production) the irritancy potential of the test items can be estimated by means of the prediction model that is composed of four broad categories (no, mild, moderate and severe irritation).

Test Items:
  Compound A: EVA40 (70%), Eudragit L (30%)
  Compound B: EVA40 (75%), Eudragit L (20%), Lactic acid (5%)
  Compound C: Lacta Gynecogel®-MedGenix (Wevelgem, BE)

Control Items:
  Neg. control solid: Drum dried waxy maize starch (DDMW)
  Pos. control solid: DDWM (80%), Sodium lauryl sulph. (20%)
  Neg. control semi-solid: Hydroxyethyl cellulose gel (5%), glycerol (2%) (HEC gel)
  Pos. control semi-solid: Hydroxyethyl cellulose gel (5%), glycerol (2%), Nonoxynol-9 (4%) (HEC/N-9 gel)

Test System:

Slugs (*Arion lusitanicus*); 5 slugs per treatment group. The parental slugs of *Arion lusitanicus* collected in local gardens along Gent and Aalter (Belgium) are bred in the laboratory in an acclimatized room (18-20° C.). The slugs are housed in plastic containers and fed with lettuce, cucumber, carrots and commercial dog food.

Test Design:

A single study was performed. Treatment time was 30 min. once a day during 5 successive days.

Experimental Design:

Preparation of the Slugs:

Slugs weighing between 3 and 6 g were isolated from the cultures two days before the start of an experiment. The body wall was inspected carefully for evidence of macroscopically injuries. Only slugs with clear tubercles and with a foot surface that showed no evidence of injuries were used for testing purposes. The slugs were placed in a plastic box lined with paper towel moistened with PBS and were kept at 18-20° C. Daily the body wall of the slugs was wetted with PBS using a micropipette.

Test Procedure Liquids:

The irritation and tissue damaging potency of the test items, negative and positive controls were evaluated by placing 5 slugs per treatment group daily during 30 min (contact period) on 20 mg (solids) or 100 mg (semi solids) of the test items for 5 successive days. After each 30-min contact period the slugs were transferred to a fresh Petri dish with a membrane filter moistened with 2 ml PBS until the next contact period. After the contact period mucus production was measured.

Determination of the Endpoints:

Mucus Production

The amount of mucus produced during each contact period was measured by weighing the Petri dishes with the test item before and after each 30-min contact period. The mucus production was expressed as % of the body weight. The slugs will be weighed before and after each 30-min contact period.

Classification Prediction Model

Based on the endpoints of the SMI assay the irritation potency of the test items defined was estimated using a classification prediction model, as depicted in table 3.

TABLE 3

Prediction model for the irritation potency of substances with a different physical state.

|  | Solid | Semi-solid |
|---|---|---|
| Non-irritant | <7% | <15% |
| Mild | 7-12% | 15-20% |
| Moderate | 12-20% | 20-25% |
| Severe | >20% | >25% |

% represent mucus production expressed as % of body weight

In particular, the irritation potency is estimated by the total mucus production, and subdivided into 4 classes (non-irritant, mild, moderate and severe irritant), of which the cut-off values depend on the physical state of the formulation (solid or semi-solid). For each slug the total mucus production was calculated by adding up to mucus produced during each 30-min contact, then the mean of the 5 slugs was calculated.

Acceptance Criteria:

Before a test can be considered valid, the following criteria must be met:
- the solid negative control (DDWM) should be classified as non-irritant (Total mucus production <7%)
- the solid positive control item (DDWM/SLS 80/20) should be classified as a severe irritant (Total mucus production >20%)
- the semi solid negative control (HEC-gel) should be classified as non-irritant (Total mucus production <15%)
- the semi solid positive control (HEC/N-9 gel) should be classified as a severe irritant (Total mucus production >25%)

Figure 1:
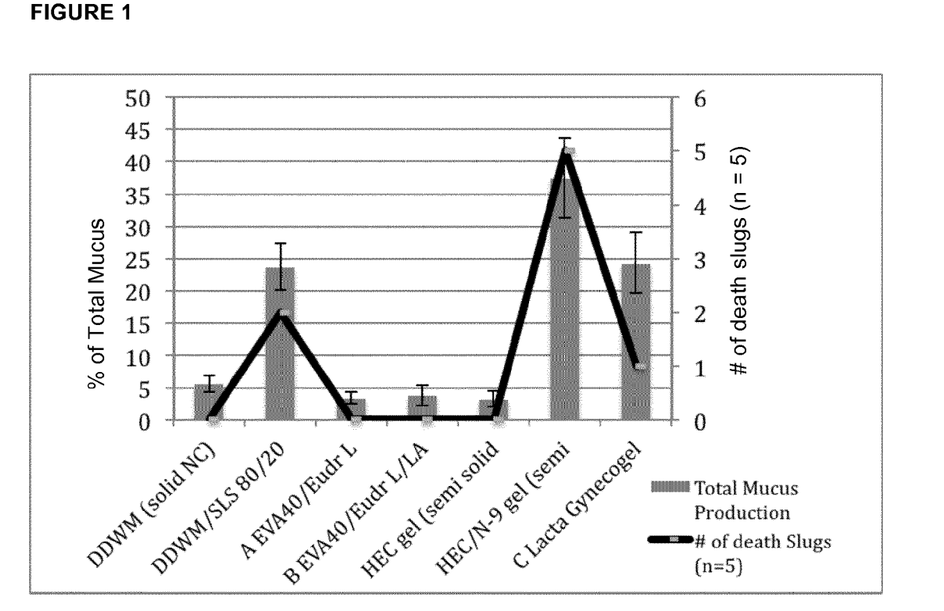
FIGS. 1 & 2: Mean mucosal production and survival of the slugs in a 5-day mucosal irritation experiment.

Results:

During 5 consecutive days, the % mucus production and the number of death slugs was determined (table 4) and at the end of the 5 day experiment, the number of death slugs as well as the mean total mucus production (MP) was calculated (FIG. 1).

First, the acceptance criteria were checked. The total MP of all the control items was according to the criteria as mentioned above, thereofore the results of this experiment are to be considered valid.

The solid negative control slugs (DDWM) produced a small amount of mucus during each contact period, and none of the slugs died from the treatment, therefore this substance was classified as causing no irritation (Total MP <7%).

Slugs treated with formulation A or B produced only a slight increased mucus production during each contact period, and again for both formulations, none of the slugs died, therefore these formulations were also classified as causing no irritation (Total MP <7%). Furthermore, total MP after 5 days was even lower than that of the solid negative control. The addition of 5% lactic acid to the formulation (B) caused only a slight increase in MP compared to formulation A without any lactic acid. Nevertheless, total MP was still <7% (cut-off between non- and slightly irritating).

The positive solid control slugs (DDWM/SLS 80/20) showed a high mucus production during the first 3 days, one slug did not survive the $3^{rd}$ contact period. Another one died after the $4^{th}$ contact period. The total MP produced by the positive control slugs was >20% indicating severe irritation to the mucosal surface of the slugs.

Three semi solid formulations were tested as well. The semi solid negative control slugs (HEC/Glycerol 5%/2%) produced only a minimal amount of mucus during each contact period, and none of the slugs died and therefore was classified as causing no irritation (Total MP <15%).

Formulation C, which is a marketed vaginal lactic acid cream containing 0.5% lactic acid (Lacta Gynecogel®) daily induced a comparable amount of mucus production, which was clearly higher than the negative control. After 5 days total MP amounted 24.3% and was therefore classified as moder-

TABLE 4

Results of a 5-day experiment

| | Mucus production (% body weight) - Survival (n/5) | | | | |
|---|---|---|---|---|---|
| Formulation | 1st 30' CP | 2nd 30' CP | 3rd 30'CP | 4th 30'CP | 5th 30'CP |
| DDWM (solid NC) | 1.1 ± 0.3 (5) | 0.8 ± 0.1 (5) | 1.0 ± 0.7 (5) | 1.2 ± 0.5 (5) | 1.5 ± 0.7 (5) |
| DDWM/SLS 80/20 (solid PC) | 5.5 ± 1.4 (5) | 8.0 ± 1.3 (5) | 6.7 ± 1.5 (5) | 2.9 ± 1.1 (4) | 2.0 ± 1.5 (3) |
| A: EVA40/Eudr L 70/30 | 0.6 ± 0.2 (5) | 0.6 ± 0.3 (5) | 0.5 ± 0.1 (5) | 0.9 ± 0.5 (5) | 0.7 ± 0.3 (5) |
| B: EVA40/Eudr L/LA 75/20/5 | 0.8 ± 0.6 (5) | 0.6 ± 0.3 (5) | 0.9 ± 0.7 (5) | 0.9 ± 0.4 (5) | 0.6 ± 0.1 (5) |
| HEC gel (semi solid NC) | 0.8 ± 0.3 (5) | 0.5 ± 0.3 (5) | 1.1 ± 0.9 (5) | 0.5 ± 0.1 (5) | 0.4 ± 0.1 (5) |
| HEC/N-9 gel (semi solid PC) | 19.7 ± 4.6 (5) | 16.0 ± 5.0 (5) | 8.6 ± 0.0 (1) | (0) | (0) |
| C: Lacta Gynecogel | 4.3 ± 0.5 (5) | 4.9 ± 0.1 (5) | 5.3 ± 1.9 (5) | 6.1 ± 3.3 (5) | 4.6 ± 1.6 (4) |

[1]Mean ± SD per contact period;
[2]Mean ± SD, n = 5;
MP: mucus produced;
% bw = % body weight;
DDWM = drum dried waxy maize starch;
NC = negative control;
SLS = sodium lauryl sulphate;
HEC gel = Hydroxyethyl cellulose gel 5% with 2% glycerol;
HEC/N-9 gel = Hydroxyethyl cellulose gel 5% with 2% glycerol and 4% Nonoxynol-9 ate irritant (Total MP between 20% and 25%). One slug did not survive the 4$^{th}$ contact period. The positive semi solid control slugs (HEC/Glycerol/N-9 5%/2%/4%) showed a high mucus production during the first 2 days, mucus production decreased substantially during the 3$^{rd}$ contact period. Four slugs did not survive the 2$^{nd}$ contact period, the last slug of this series died after the 3$^{rd}$ contact period. The total MP produced by the positive control slugs was >25% indicating severe irritation to the mucosal surface of the slugs.

Conclusion:

Solid formulations A and B induced only minor reactions in slugs, and they were even better tolerated than the solid negative control. Reactions of the marketed vaginal lactic acid cream Lacta Gynecogel® were much more pronounced, and resulted in a classification as a moderate irritant.

Example 4

Slug Irritation Test

In this example, 2 additional compositions comprising EVA40/Eudragit L and lactic acid were tested and compared to the 75/20/5 composition as used in example 3. The study outline, control items, test system, . . . were as described in example 3.

Figure 2:
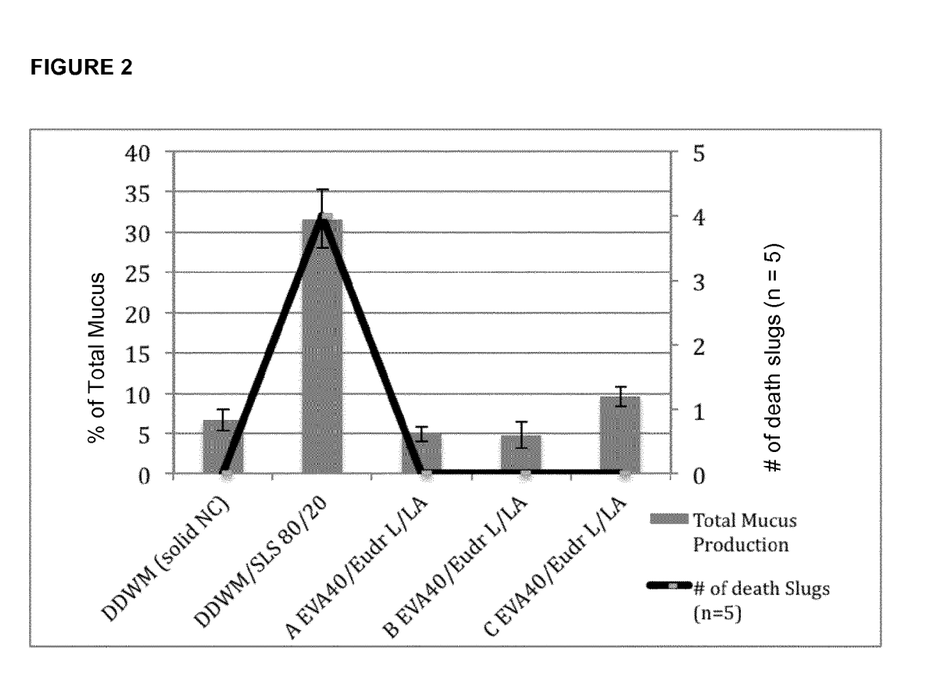

Results:

During 5 consecutive days, the % mucus production and the number of death slugs was determined (table 5) and at the end of the 5 day experiment, the number of death slugs as well as the mean total mucus production (MP) was calculated (FIG. 2).

Test Items:
 Compound A: EVA40 (75%), Eudragit L (20%), Lactic acid (5%)
 Compound B: EVA40 (72.5%), Eudragit L (20%), Lactic acid (7.5%)
 Compound C: EVA40 (70%), Eudragit L (20%), Lactic acid (10%)

First, the acceptance criteria were checked. The total MP of all the control items was according to the criteria as mentioned above, therefore the results of this experiment are to be considered valid.

The solid negative control slugs (DDWM) produced a fairly small amount of mucus during each contact period, and none of the slugs died from the treatment, therefore this substance was classified as causing no irritation (Total MP <7%).

The positive solid control formulation (DDWM/SLS 80/20) showed the highest mucus production during all 5 days. One slug did not survive the 3$^{rd}$ contact period, three other slugs died after the 4$^{th}$ contact period. The total MP was >20% indicating severe irritation to the mucosal surface of the slugs.

Slugs treated with formulation A or B produced only a slight increased mucus production during each contact period, and again for both formulations, none of the slugs died, therefore these formulations were also classified as causing no irritation (Total MP <7%).

Slugs treated with formulation C, containing the highest concentration of lactic acid tested (i.e. 10%), induced a more pronounced reaction in the slugs, with a total MP >7%, but still <12%, however, again none of the slugs died, therefore this formulations were classified as causing mild irritation.

Conclusion:

Formulations A and B induced only minor reactions in slugs, and they were even better tolerated than the solid negative control. Formulation C, containing 10% lactic acid, induced a higher mucus production than formulations A and B, but was still classified as causing only mild irritation.

References

Adriaens, E. and Remon, J. P. (1999). Gastropods as an evaluation tool for screening the irritating potency of absorption enhancers and drugs. *Pharm. Res.* 16: 1240-1244.

Adriaens, E., Dierckens, K., Bauters, T. G. M., Nelis, H. J., Van Goethem, F., Vanparys, P. and Remon, J. P. (2001). The mucosal toxicity of different benzalkonium chloride analogues with an alternative test using slugs. *Pharm. Res.* 18: 937-942

Adriaens E. and Remon J. P. (2002). The evaluation of an alternative mucosal irritation test using slugs. *Tox. Appl. Pharm.* 182: 169-175

TABLE 5

Results of a 5-day experiment

| Formulation | Mucus production (% body weight) - Survival (n/5) | | | | |
|---|---|---|---|---|---|
| | 1st 30' CP | 2nd 30' CP | 3rd 30'CP | 4th 30'CP | 5th 30'CP |
| DDWM (solid NC) | 1.1 ± 0.2 (5) | 1.4 ± 0.6 (5) | 1.6 ± 0.6 (5) | 1.5 ± 0.6 (5) | 1.1 ± 0.3 (5) |
| DDWM/SLS 80/20 (solid PC) | 6.7 ± 1.1 (5) | 7.3 ± 1.0 (5) | 10.3 ± 4.3 (5) | 6.3 ± 3.0 (4) | 11.1 ± 0.0 (1) |
| A: EVA40/Eudr L/LA 75/20/5 | 1.4 ± 0.6 (5) | 1.0 ± 0.5 (5) | 1.0 ± 0.5 (5) | 1.0 ± 0.3 (5) | 0.6 ± 0.2 (5) |
| B: EVA40/Eudr L/LA 72.5/20/7.5 | 1.0 ± 0.3 (5) | 1.0 ± 0.4 (5) | 1.0 ± 0.6 (5) | 0.9 ± 0.4 (5) | 0.7 ± 0.3 (5) |
| C: EVA40/Eudr L/LA 70/20/10 | 2.2 ± 0.8 (5) | 1.5 ± 0.2 (5) | 1.9 ± 0.3 (5) | 2.3 ± 0.4 (5) | 1.7 ± 0.8 (5) |

[1]Mean ± SD per contact period;
[2]Mean ± SD, n = 5;
MP: mucus produced;
% bw = % body weight;
DDWM = drum dried waxy maize starch;
NC = negative control;
PC = positive control Adriaens, E., Ameye, D., Dhondt, M. M. M., Foreman, P. and Remon, J. P. (2003). Evaluation of the mucosal irritation potency of co-spray dried Amioca/Poly(Acrylic Acid) and Amioca/Carbopol 974P mixtures. *J. Control. Release.* 88(3): 393-399

Adriaens, E., Dhondt, M. M. M. and Remon, J. P. (2005). Refinement of the Slug Mucosal Irritation test as an alternative screening test for eye irritation. *Toxicol. in Vitro* 19(1): 79-89

Adriaens, E., Bytheway, H, De Wever, B., Eschrich, D., Guest, R., Hansen, E., Vanparys, P, Schoeters, G., Warren, N., Weltens, R., Whittingham, A., Remon, J. P. (2008). Successful prevalidation of the slug mucosal irritation test to assess the eye irritation potency of chemicals *Toxicol. in Vitro in press*

Andersch B., Lindell D., Brandberg A., (1990) Bacterial Vaginosis and the effect of intermittent prophylactic treatment with an acid lactate gel. *Gynacol Obstet Invest* 30: 114-119

Argemi A., Ellis J. L., Saurina J., Tomasko D. L. (2011). Development of a polymeric patch impregnated with naproxen as a model of transdermal sustained release system. *J. Pharm Sci* 100:992-1000

Bhatt H. R., Gurnasinghani M. L., Dattani K. K., Lalla J. K. (1989). Controlled release nitroglycerin capsules. *J. of Controlled Release* 9(1) 43-55.

Boskey E. R., Cone R. A., Whaley K. J., Moench T. R. (2001). Origins of vaginal acidity: high D/L lactate ratio is consistent with bacteria being the primary source. *Human Reproduction* 16(9) 1809-1813.

Callens, C., Adriaens, E., Dierckens, K. and Remon, J. P. (2001). Toxicological evaluation of a bioadhesive nasal powder containing a starch and carbopol 974 p on rabbit nasal mucosa and slug mucosa. *J. Control. Rel.* 76: 81-91.

Ceulemans J., Vermeire A., Adriaens E., Remon J. P. and Ludwig A. (2001). Evaluation of a mucoadhesive tablet for ocular use. *J. Control. Release.* 77: 333-344

Dhondt, M. M. M., Adriaens, E. and Remon, J. P. (2004). The Evaluation of the local tolerance of vaginal formulations, with or without Nonoxynol-9, using the Slug Mucosal Irritation test. *Sex. Trans. Dis.* 31(4): 229-235

Dhondt, M. M. M., Adriaens, E., Van Roey, J., and Remon, J. P (2005). Evaluation of the local tolerance of vaginal formulations containing TMC 120 using rabbits and slugs. *Eur. J. Pharm. Biopharm.* 60: 419-425.

Dhondt, M. M. M., Adriaens, E., Pinceel, J., Jordeans, K., Backeljau, T. and Remon J. P. Slug species and populations specific effects on the end points of the Slug Mucosal Irritation test. *Toxicology in vitro* (Accepted September 2005)

Draize, J. H., Woodward, G. and Calvery, H. O. (1944). Methods for the study of irritation and toxicity of substances applied to the skin and mucous membranes. *J. Pharmacol. Exp. Ther.* 82: 377

Harvey, M. D., Bablekis, V., Banks, P. R., and Skinner, C. D. (2001). Utilization of the non-covalent fluorescent dye, NanoOrange, as a potential clinical diagnostic tool—Nanomolar human serum albumin quantitation. *J. Chromatogr. B* 754: 345-356.

Weyenberg, W., Vermeire, A., Dhondt, M. M. M, Adriaens, E., Kestelyn, P., Remon, J. P. and Ludwig, A. (2004) Ocular bioerodible minitablets as strategy for the management of microbial keratitis. *Investigative Ophthalmology & Visual Science.* 45(9): 3229-3233.

The invention claimed is:

1. A controlled release intravaginal delivery system for controlled release of one or more liquid carboxylic acids with a $pK_a$ of less than 6, the controlled release intravaginal delivery system comprising:
   the one or more liquid carboxylic acids with a $pK_a$ of less than 6; and
   a combination of one or more ethylene vinyl acetate (EVA) copolymers and one or more carboxylic non-cationic polymers, wherein the one or more carboxylic non-cationic polymers are selected from the group consisting of methacrylic acid copolymers, cellulose acetate phthalates (CAP), acrylic acid copolymers, alginates, hypromellose acetate succinates (HPMCAS), and copolymers or mixtures thereof, and wherein the controlled release intravaginal delivery system controllably releases the one or more liquid carboxylic acids with a $pK_a$ of less than 6 therefrom upon administration thereof.

2. The controlled release intravaginal delivery system according to claim 1, wherein the one or more EVA copolymers are copolymers of ethylene and vinyl acetate comprising about 25 to 40% vinyl acetate.

3. The controlled release intravaginal delivery system according to claim 1 comprising a combination of one or more EVA polymers and one or more methacrylic acid copolymers.

4. The controlled release intravaginal delivery system according to claim 1, wherein the one or more liquid carboxylic acids with a $pK_a$ of less than 6 are selected from the group consisting of lactic acid, polylactic acid, glycolic acid, polyglycolic acid, folic acid, p-aminobenzoic acid, alginic acid, sorbic acid, tartaric acid, acetic acid, formic acid, citric acid, oxalic acid, edetic acid, adipic acid, succinic acid, glutamic acid; and mixtures thereof.

5. The controlled release intravaginal delivery system according to claim 1, comprising about 1-20% wt of said one or more liquid carboxylic acids with a $pK_a$ of less than 6.

6. The controlled release intravaginal delivery system according to claim 1, comprising about 65-80% wt of one or more EVA polymers and about 10-50% wt of one or more carboxylic non-cationic polymers.

7. The controlled release intravaginal delivery system according to claim 1, comprising about 1-20% wt lactic acid; about 65-80% wt EVA; and about 10-50% wt of one or more carboxylic non-cationic polymers.

8. The controlled release intravaginal delivery system according to claim 1, further comprising one or more pharmaceutically active ingredients.

9. A method of treating vaginal infections, said method comprising administering to a patient in need thereof the controlled release intravaginal delivery system according to claim 1.

10. A method for the controlled intravaginal delivery of one or more liquid carboxylic acids with a $pK_a$ of less than 6 comprising the administration of the controlled release intravaginal delivery system according to claim 1.

11. The method according to claim 9 wherein said controlled release intravaginal delivery system is administered in combination with one or more additional pharmaceutically active agents.

12. The intravaginal delivery system of claim 1 having an annular shape, ring shape, oval, spiral, elliptical, or toroidal shape.

13. A controlled release intravaginal delivery system for controlled release of one or more liquid carboxylic acids with a $pK_a$ of less than 6, the controlled release intravaginal delivery system comprising:

about 1-20% wt of the one or more liquid carboxylic acids with a $pK_a$ of less than 6 selected from the group consisting of lactic acid and acetic acid; and     a combination of about 65-80% wt of one or more ethylene vinyl acetate (EVA) copolymers and about 10-50% wt of one or more carboxylic acids selected from the group consisting of methacrylic acid copolymers, methacrylic ester copolymers, and cellulose acetate phthalates (CAP), wherein the controlled release intravaginal delivery system controllably releases the one or more liquid carboxylic acids with a $pK_a$ of less than 6 therefrom upon administration thereof.

14. The controlled release intravaginal delivery system of claim 13, comprising:

about 5-10% wt of the one or more liquid carboxylic acids with a $pK_a$ of less than 6;

about 70-75% wt of the one or more EVA; and about 20% wt of the one or more carboxylic acids.

15. The controlled release intravaginal delivery system of claim 13, comprising:

about 5-10% wt of lactic acid;

about 70-75% wt of the one or more EVA; and about 20% of methacrylic acid copolymer L.

16. The controlled release intravaginal delivery system of claim 13, comprising:

about 5-10% wt of acetic acid;

about 70-75% wt of the one or more EVA; and about 20% of CAP.

\* \* \* \* \*

UNITED STATES PATENT AND TRADEMARK OFFICE
CERTIFICATE OF CORRECTION

PATENT NO. : 9,168,303 B2  
APPLICATION NO. : 14/131495  
DATED : October 27, 2015  
INVENTOR(S) : Jean Paul Remon et al.

Page 1 of 1

It is certified that error appears in the above-identified patent and that said Letters Patent is hereby corrected as shown below:

In the Specification

Col. 2, Line 65,
"relevant levels of organic acids in a certain polymeric envi-" should read
--relevant levels of organic acids in certain polymeric envi- --;

Col. 7, Line 11,
"Therefore, a mixtures of 75%-wt ethylene vinyl acetate" should read
--Therefore, mixtures of 75%-wt ethylene vinyl acetate--;

Col. 8, Line 53,
"3. After 24 u the pH was measured and the medium was" should read
--3. After 24 h the pH was measured and the medium was--;

Col. 12, Line 3,
"tioned above, thereofore the results of this experiment are to" should read
--tioned above, therefore the results of this experiment are to--; and Col. 14, Line 25,
"this formulations were classified as causing mild irritation." should read
--these formulations were classified as causing mild irritation.--.

Signed and Sealed this  
Twenty-eighth Day of June, 2016

Michelle K. Lee  
*Director of the United States Patent and Trademark Office*